United States Patent [19]
Mason et al.

[11] Patent Number: 5,324,319
[45] Date of Patent: Jun. 28, 1994

[54] GRAVITY DRIVEN THERAPEUTIC FLUID CIRCULATION DEVICE

[75] Inventors: Jeffrey T. Mason, Escondido; Bradley R. Mason, Olivenhain, both of Calif.

[73] Assignee: Breg, Inc., Vista, Calif.

[21] Appl. No.: 906,407

[22] Filed: Jul. 1, 1992

Related U.S. Application Data

[63] Continuation-in-part of Ser. No. 767,494, Sep. 30, 1991, Pat. No. 5,241,951, and a continuation-in-part of Ser. No. 578,508, Sep. 5, 1990, Pat. No. 5,080,089.

[51] Int. Cl.$^5$ ............................................. A61F 7/00
[52] U.S. Cl. ........................................ 607/104; 607/96; 607/112
[58] Field of Search ............... 128/24, 24.1, 400, 402; 607/96, 104, 112

[56] References Cited

U.S. PATENT DOCUMENTS

| | | | |
|---|---|---|---|
| 267,435 | 11/1882 | Leiter | 128/400 X |
| 500,568 | 7/1893 | Ells | 128/402 |
| 691,270 | 1/1902 | Jones | 128/400 X |
| 787,920 | 4/1905 | Hofmann . | |
| 1,004,192 | 9/1911 | Phelan . | |
| 1,011,606 | 12/1911 | Fulton | 128/400 |
| 1,622,903 | 3/1927 | Cox . | |
| 1,636,568 | 7/1927 | Kennedy | 128/402 X |
| 1,640,014 | 8/1927 | Tomasulo . | |
| 2,026,747 | 1/1936 | Nemzek . | |
| 3,017,888 | 1/1962 | Weiner . | |
| 3,247,851 | 4/1966 | Seibert . | |
| 3,683,902 | 8/1972 | Artemenko et al. . | |
| 5,106,373 | 4/1992 | Augustine et al. . | |
| 5,170,783 | 12/1992 | Smith | 128/400 |
| 2,726,6587 | 12/1955 | Chessey | 128/402 X |

Primary Examiner—Robert Bahr
Attorney, Agent, or Firm—Rodney F. Brown

[57] ABSTRACT

A device for therapeutically treating a desired region of a patient's body with a nonambient temperature fluid includes a fluid feed reservoir, a fluid collection reservoir, and a fluid flowpath therebetween. The flowpath is made up of a heat transfer pad placed over the desired treatment region, an inlet line leading from the feed reservoir to the pad, and an outlet line leading from the pad to the collection reservoir. In operation, the feed reservoir is charged with a nonambient temperature fluid and maintained at a height substantially greater than the height of the collection reservoir to provide a fluid head sufficient to transport the fluid from the feed reservoir to the collection reservoir across the flowpath. In so doing, the pad provides therapeutic treatment to the region of the body that it contacts. The temperature of the pad is controlled by maintaining a height differential between the fluid levels in the feed reservoir and the collection reservoir.

13 Claims, 2 Drawing Sheets

GRAVITY DRIVEN THERAPEUTIC FLUID CIRCULATION DEVICE

This application is a continuation-in-part patent application of our prior co-pending patent application entitled, "Therapeutic Nonambient Temperature Fluid Circulation System", Ser. No. 767,494 filed on Sep. 30, 1991, now patent No. 5,241,951 which is a continuation-in-part application of our patent application entitled, "Therapeutic Apparatus Applying Compression and a Nonambient Temperature Fluid," Ser. No. 578,508 filed on Sep. 5, 1990 and now issued as U.S. Pat. No. 5,080,089.

TECHNICAL FIELD

The present invention relates generally to therapeutic treatment of the body and more particularly to an apparatus for treating bodily injuries and ailments by cooling or heating the affected region of the body with a nonambient treatment fluid circulated through a pad positioned on the affected region.

BACKGROUND OF THE INVENTION

Bodily injuries and ailments are commonly treated by applying a nonambient temperature material to the affected area of the body. For example, low temperature material, typically in the form of ice or a cold liquid, advantageously inhibits swelling in the region of the injury. A high temperature material, typically applied in the form of hot water or an active heating element, advantageously reduces pain and promotes healing.

A number of devices have been developed for circulating a cooling fluid from a low temperature reservoir to a desired body location. Such devices are typified by U.S. Pat. Nos. 2,726,658 to Chessey; 3,683,902 to Artemenko et al; and 4,962,761 to Golden. These devices are noteworthy in that they are relatively complex and thus, costly to manufacture and maintain, as well as being somewhat difficult to operate. Accordingly, the systems are not particularly practical for use among the general population.

Given the proliferation of sports and leisure activities and the proliferation of injuries associated therewith, a widespread need exists for a practical therapeutic nonambient temperature treatment device. In particular, a need exists for a device which circulates a nonambient temperature fluid across a desired surface of the body to provide therapeutic treatment thereto, wherein the device is relatively simple to operate and inexpensive to produce and maintain. As such a therapeutic nonambient treatment device is needed which can be employed in the home or in the workplace to provide cost-effective treatment which does not significantly disrupt the daily schedule of the user.

SUMMARY OF THE INVENTION

The present invention is a device for therapeutically treating a desired region of a patient's body with a nonambient temperature fluid, i.e., a cooling fluid or a heating fluid. The fluid is circulated through the device under the force of gravity from a fluid feed reservoir to a fluid collection reservoir. The flowpath between the two reservoirs comprises a heat transfer pad placed over the desired treatment region, a fluid inlet line leading from the fluid feed reservoir to the pad, and a fluid outlet line leading from the pad to the fluid collection reservoir.

The pad encloses a continuous tortuous pathway for the nonambient temperature fluid and has a fluid inlet port at its entrance and a fluid outlet port at its exit. One end of the fluid inlet line is connected to the inlet port of the pad and the other end is connected to an outlet port of the fluid feed reservoir. Similarly, one end of the fluid outlet line is connected to the outlet port of the pad and the other end is connected to the inlet port of the fluid collection reservoir.

The fluid feed reservoir is initially charged with a nonambient temperature fluid and is maintained at a height substantially greater than the height of the fluid collection reservoir. The height differential establishes a fluid head between the fluid-filled feed reservoir and the collection reservoir. The fluid head provides a sufficient gravitational driving force to transport the nonambient temperature fluid from the fluid feed reservoir to the fluid collection reservoir.

In operation, the fluid feed reservoir drains while the fluid collection reservoir simultaneously fills. In so doing, the nonambient temperature fluid passes through the tortuous pathway of the pad, providing therapeutic treatment to the desired region of the body. Once the fluid feed reservoir is completely drained, the positions of the two reservoirs are reversed such that the fluid collection reservoir, which is now filled with nonambient temperature fluid, becomes the elevated fluid feed reservoir and the previous fluid feed reservoir becomes the lower fluid collection reservoir.

Cycling of the reservoirs can be repeated as long as treatment is desired and as long as the fluid maintains a desired nonambient temperature. When the fluid approaches ambient temperature the device can be recharged with a new nonambient temperature fluid or, in the case of a cold temperature treatment, the life of the cooling fluid can be extended by charging ice to either or both reservoirs.

The reservoirs are essentially identical in construction, each being a pouch formed from a pliable collapsible material that is watertight. The ports are formed at or near the bottom of each pouch and a sealable opening is provided near the top of each pouch that enables access to the pouch for the addition or withdrawal of materials therefrom, such as ice or fluid.

The temperature of the pad can be controlled by adjusting the height differential between the fluid feed reservoir and the fluid collection reservoir. For this purpose, the device is provided with a stand and a pair of cords of adjustable length, each cord being attached to a reservoir. The reservoirs are maintained at their desired height differential by suspending them from the stand either directly or by their cords. If it is desirable to raise the temperature of a cooling fluid or lower the temperature of a heating fluid, the length of one or both of the cords is adjusted to reduce the height differential between the reservoirs, thereby slowing the fluid flow rate through the pad.

In the preferred embodiment, automatic adjustment of the cord length is provided to maintain a relatively fixed height differential between the fluid levels in the two reservoirs. Each cord is highly elastic which enables it to stretch under the weight of its respective reservoir. Thus, as the volume of fluid in the reservoir changes, the weight of the reservoir changes causing the cord attached thereto to stretch or contract. In this manner, the cord automatically adjusts the height of the reservoir. The device is designed such that changes in the volume, weight and height of the reservoirs offset each other to achieve a relatively fixed fluid level height differential between the two reservoirs throughout the operation of the device.

The cords also facilitate cycling of the reservoirs when the fluid feed reservoir is emptied. Cycling is achieved simply by raising the fluid-filled collection reservoir onto the stand off of its cord and lowering the empty feed reservoir onto its cord from the stand so that the collection reservoir is elevated over the feed reservoir, and is thus transformed into the feed reservoir of the next treatment cycle.

The present invention will be further understood, both as to its structure and operation, from the accompanying drawings, taken in conjunction with the accompanying description, in which similar reference characters refer to similar parts.

DESCRIPTION OF PREFERRED EMBODIMENTS

Figure 1:
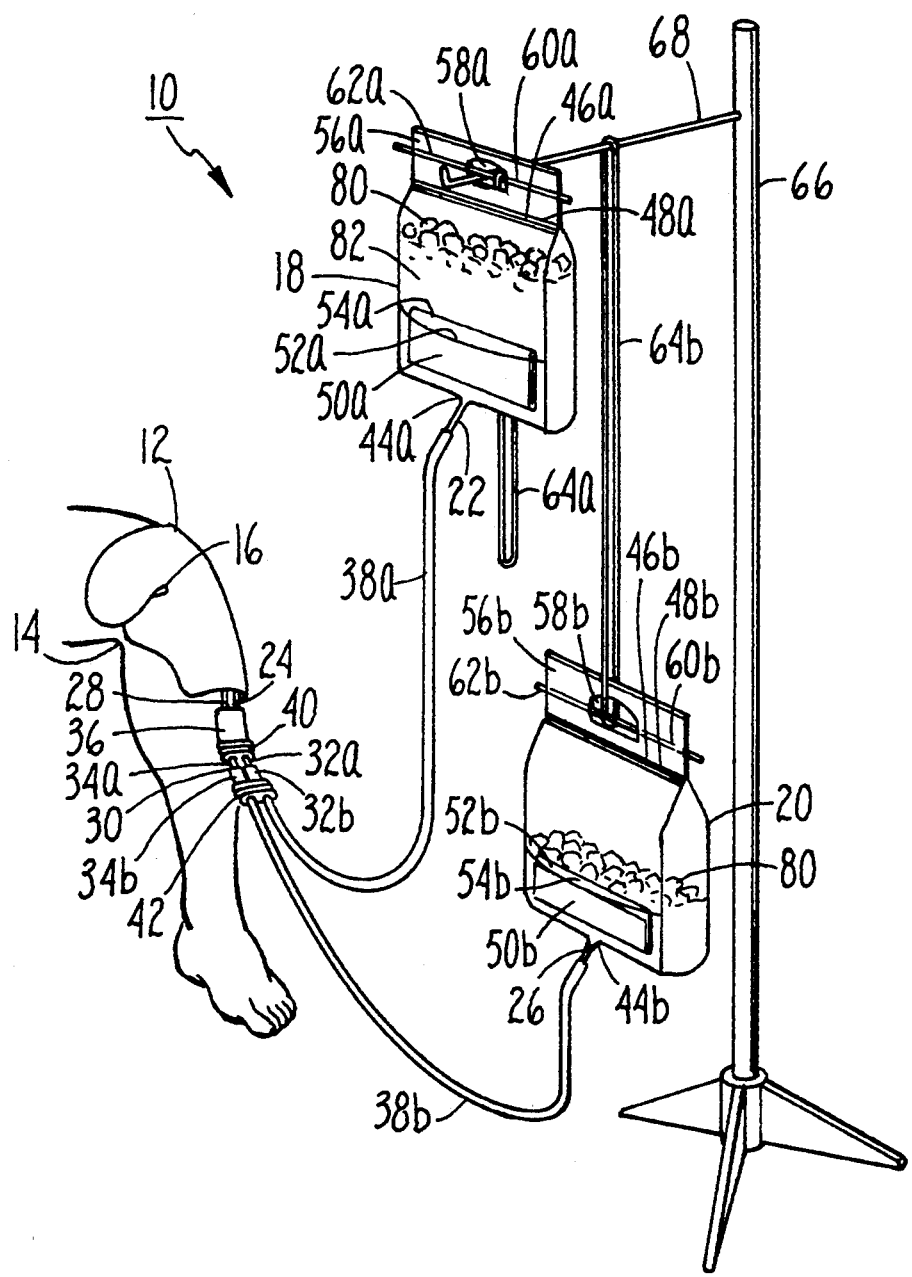
FIG. 1 is a perspective view of the therapeutic fluid circulation device of the present invention in an operational environment.

Referring initially to FIG. 1, the therapeutic fluid circulation device of the present invention is shown and generally designated as 10. For purposes of illustration, the specific device shown in FIG. 1 is a low temperature embodiment of the present invention. The description of the low temperature embodiment set forth below, however, is generally applicable to all nonambient temperature embodiments of the present invention.

Figure 2:
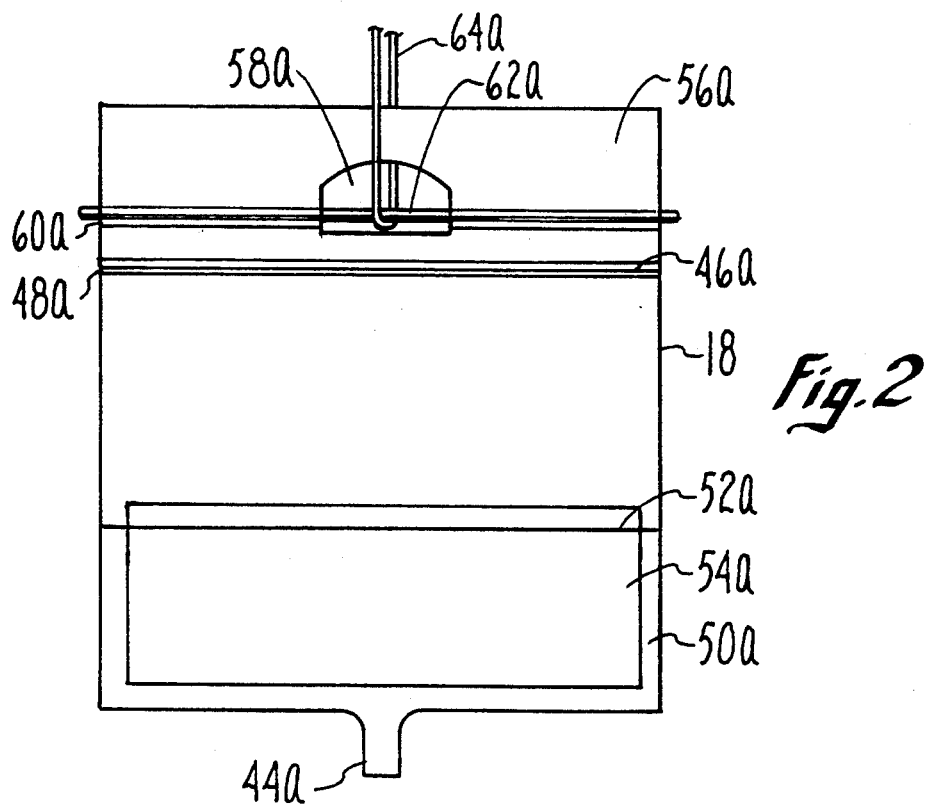
FIG. 2 is a front view of a reservoir as used in the therapeutic fluid circulation device of the present invention.

Device 10 comprises a cooling pad 12 positionable on the body of a patient in the region where therapeutic low temperature treatment is desired. Pad 12 is shown positioned on the knee 14, but pad 12 can be positioned substantially anywhere on the body where treatment is desired. Pad 12 is fabricated from a pliable material that is conformable to the body contours of the patient. To facilitate conformance, pad 12 has one or more notches 16 formed therein which enable pad 12 to overlap the irregular contours of the body. The configuration of pad 12 and its associated fittings is described hereafter in greater detail with reference to FIG. 2.

Referring further to FIG. 1, device 10 additionally comprises a fluid feed reservoir 18 and a fluid collection reservoir 20. Fluid feed reservoir 18 is in fluid communication with pad 12 across fluid inlet line 22 and pad inlet port 24. Similarly, fluid collection reservoir 20 is in fluid communication with pad 12 across fluid outlet line 26 and pad outlet port 28. Each line 22 and 26 is preferably on the order of about 6 feet in length. Lines 22 and 26 and ports 24 and 28 are releasably connected at joint 30 and each preferably has an inside diameter of about ⅛ inches. Joint 30 comprises a first male/female coupling pair 32a, 32b and a second, male/female coupling pair 34a, 34b.

Pad inlet and outlet ports 24, 28 are enclosed in a common insulative sheath 36 leading into joint 30, and fluid inlet; and outlet lines 22, 26 are enclosed in individual insulative sheaths 38a, 38b leading into joint 30. Insulative sheaths 36, 38a, 38b are preferably formed from a flexible insulative foam material. Also provided at joint 30 are grips 40 and 42 facilitating connection and disconnection of joint 30, Grip 40 and male couplings 32a and 34a are preferably formed integral with one another from a rigid DELRIN plastic. Grip 42 and female couplings 32b and 34b are also preferably formed integral with one another from a same rigid plastic. Lines 22 and 26 are preferably formed from a conventional flexible plastic tubing material.

Reservoir 18 is a collapsible pouch formed from a transparent, pliable and watertight plastic material. Reservoir 18 is described in greater detail with reference to FIG. 2, wherein a reservoir fluid outlet port 44a is shown at the bottom of reservoir 18. The reservoir fluid outlet port 44a is a short spout integral with reservoir 18 and compression fitted into inlet line 22. The top of reservoir 18 has a resealable opening 46a which enables the placement or withdrawal of materials therefrom. FIG. 1 shows opening 46a in a sealed state. Unsealing and resealing of opening 46a is provided by any number of conventional closures known in the art, such as a plastic tongue and groove type closure 48a commonly available under the mark, ZIPLOC.

A pocket 50a having an open top 52a extends the length of the bottom of reservoir 18 and is sized to retain an absorbent material 54a, such as paper toweling, therein which absorbs any condensate forming on the outside of reservoir 18 and dripping down into pocket 50a. A reinforced tab 56a extends along the top of reservoir 18 and has an aperture 58a formed therethrough at its center. A sleeve 60a extends lengthwise through tab 56a and is so positioned to slidably receive a rigid reinforcement member 62a therein. Reinforcement member 62a is preferably a rigid metal rod.

Aperture 58a intersects with sleeve 60a such that reinforcement member 62a is accessible to the outside at aperture 58a. Accordingly, an elastic cord loop 64a, such as a common bungee cord, is threaded through aperture 58a and around support member 62a from which reservoir 18 can be suspended in a manner that provides for automatic adjustment of the length of cord 64a and consequently adjustment of the height of suspended reservoir 18 as described hereafter. Alternatively, reservoir 18 can be suspended by support member 62a at a fixed height as further described hereafter.

Referring now back to FIG. 1, fluid collection reservoir 20 is shown to have a construction substantially identical to that of fluid feed reservoir 18. Thus, the above-recited description with respect to fluid feed reservoir 18 applies likewise to fluid collection reservoir 20. Fluid collection reservoir 20 is provided with a reservoir fluid inlet port 44b, an opening 46b, a closure 48b, a pocket 50b, a tab 56b, an aperture 58b, a sleeve 60b, a reinforcement member 62b and cord 64b in the same manner as reservoir 18.

A stand 66 can further be provided as an associated component of device 10. Stand 66 can be any stationary structure capable of supporting reservoirs 18 and 20. Stand 66 shown here is a conventional free-standing structure commonly used in hospitals as an intravenous fluid (IV) stand. Both reservoirs 18 and 20 are suspended from a hanger 68 on stand 66, fluid feed reservoir 18 being suspended by reinforcement member 62a and fluid collection reservoir 20 being suspended by cord 64b respectively.

It is shown that fluid collection reservoir 20 is suspended from stand 66 at a height substantially lower than the height of fluid feed reservoir 18. The height differential between the two suspended reservoirs 18 and 20 is achieved, as noted above, by freely suspending fluid collection reservoir 20 from cord 64b at a height varying according to the elasticity of cord 64b and the weight of reservoir 20, while suspending fluid feed reservoir 18 by reinforcement member 62a at a fixed height with cord 64a dangling freely from reinforcement member 62a. Cords 64a and 64b are each about 12 inches long in an unstretched condition and stretches further under the weight their respective reservoirs 18 and 20.

Figure 3:
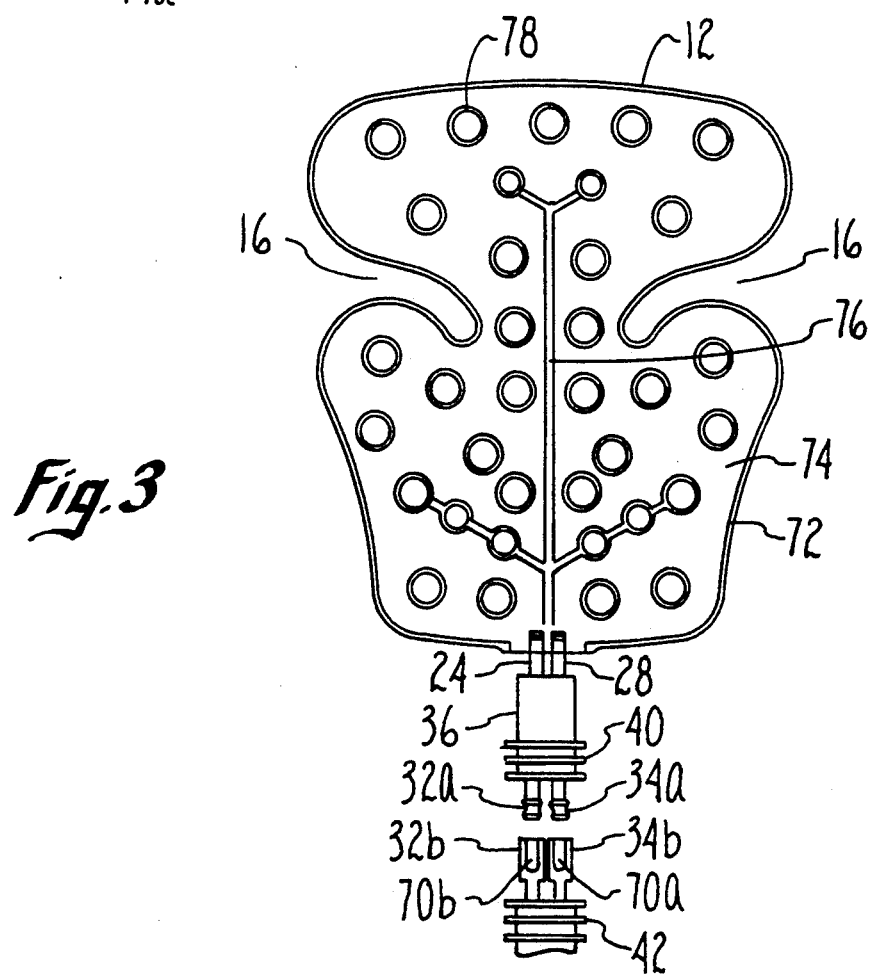
FIG. 3 is a bottom view of a heat transfer pad in the therapeutic fluid circulation device of the present invention.

Referring to FIG. 3, the construction of pad 12 and its associated fittings is described in more detail. The view of pad 12 in FIG. 3 is reversed from that of FIG. 1 to clearly show the fluid pathway on the backside of pad 12 which, in operation, is positioned away from view against the body of the patient. In addition to the components of joint 30 described above, lock release buttons 70a, 70b are provided on female couplings 32b, 34b which enable dissociation of joint 30 when depressed.

Pad 12 is preferably fabricated from two sheets of pliable polyurethane film that are welded together around their perimeter 72 to form an internal flow chamber 74. A pliable foam sheet may also be laminated to the front of pad 12 for insulative purposes. A plurality of linear and circular flow diverters 76 and 78 are positioned within flow chamber 74 which establish a tortuous pathway for fluid flow through pad 12. Flow diverters 76, 78 are formed by welding the two sheets of polyurethane film together at the desired location of the diverters.

METHOD OF OPERATION

Operation of therapeutic fluid circulation device 10 is initiated by unsealing closures 48a, 48b and placing ice 80 in reservoirs 18, 20 through openings 46a, 46b. Fluid feed reservoir 18 is also charged with cold water 82 which serves as the nonambient temperature fluid of device 10. Closures 48a, 48b are then resealed. With joint 30 secured, pad 12 is placed on the skin of the patient where therapeutic treatment is desired. An additional padding material, such as a soft cloth, may be placed on the skin for the comfort of the patient.

Reservoirs 18, 20 are then suspended from hanger 68 by reinforcement member 62a and cord 64b respectively. Cord 64b is preselected with a given elasticity such that reservoir 20 descends to a desired height under its own weight, the desired height being below that of fluid feed reservoir 18. The height differential between the two reservoirs 18, 20 is most meaningfully expressed in terms of the height differential between the respective fluid levels in the two reservoirs at any given time. A preferred fluid level height differential is between about 10 and 30 inches and more preferably between about 16 and 24 inches.

The fluid level height differential provides a fluid head between fluid feed reservoir 18 and fluid collection reservoir 20 which enables gravity to drive cold water 82 from fluid feed reservoir 18 to fluid collection reservoir 20 through pad 12. In so doing, pad 12 cools the region of the body that it contacts.

As fluid collection reservoir 20 fills, its weight increases causing cord 64b to stretch further, thereby continuously lowering reservoir 20. However, the fluid level in reservoir 20 increases as reservoir 20 descends. Simultaneously, the fluid level in reservoir 18 decreases while reservoir 18 remains static on hanger 68. The rates of change in fluid levels coupled with the rate of descent of reservoir 20 all offset each other to maintain the fluid level height differential between the two reservoirs 18, 20 substantially constant within the above-prescribed range.

When fluid feed reservoir 18 is finally depleted of cold water 82, it is removed from static suspension by reinforcement member 62 on hanger 68 and dynamically suspended from elastic cord 64a. Conversely, fluid collection reservoir 20 is removed from dynamic suspension by cord 64b and statically suspended from hanger 68 by reinforcement member 62b. Having reversed the positions of reservoirs 18 and 20 to establish a fluid head therebetween, the next cooling cycle is initiated. In this cooling cycle, reservoir 20 is the fluid feed reservoir, discharging cold water 82 under the force of gravity through pad 12 to reservoir 18, which is the fluid collection reservoir.

The temperature of the fluid in device 10 may be regulated during operation by adjusting the fluid flow rate through pad 12. To raise the low temperature of the cooling fluid, the flow rate is decreased, and conversely to maintain the low temperature of the cooling fluid, the flow rate is increased. Since the flow rate is directly related to the height differential between the fluid feed reservoir and the fluid collection reservoir, in practice the height differential is increased to raise the low temperature of the cooling fluid, while it is decreased to maintain the low temperature of the cooling fluid.

Although the fluid level height differential is maintained automatically at an optimum value by the present configuration of cords 64a, 64b, the differential can be altered manually simply by looping the desired cord onto itself and knotting it to reduce its length. Alternatively, the fluid level height differential can be reduced by suspending both reservoirs 16, 18 by their cords 64a, 64b from the stand 66 simultaneously. In any event, a fluid flow rate is preferably selected such that the temperature in the pad 12 during a low temperature treatment is maintained within a range from about 40° F. to about 55° F.

The fixed parameters of device 10 also impact the fluid flow rate, and include the length and diameter of fluid lines 22, 26. Thus, flow rates can also be controlled prior to operation of device 10 by preselecting the geometry of fluid lines 22, 26. Alternatively, flow restrictors can be placed in flow lines 22, 26 or ports 24, 28, 44a, 44b to modify the fluid flow rate. Given the prescribed fixed parameters of lines 22, 26, and the preferred range of the fluid level height differential set forth above, a fluid flow rate of about 4 ounces per minute is achieved in device 10 which has been found sufficient to obtain the desired level of cooling during a low temperature treatment.

The high temperature embodiment of the therapeutic fluid circulation device of the present invention is distinguishable from the low temperature embodiment in that a heated fluid is substituted for the cooling fluid of reservoir 18 and no ice is added to reservoir 18 or 20. In operation, the high temperature of the heating fluid is decreased by decreasing the flow rate while the high temperature is maintained by increasing the flow rate. Thus, in contrast to the low temperature embodiment, the height differential is decreased to lower the high temperature of the heating fluid, while it is increased to maintain the high temperature of the heating fluid.

While the particular gravity driven therapeutic fluid circulation device as herein shown and disclosed in detail is fully capable of obtaining the objects and providing the advantages hereinbefore stated, it is to be understood that this device is merely illustrative of the presently preferred embodiments of the invention and that other embodiments are possible within the scope of the present invention.

We claim:

1. A device for therapeutically treating a desired portion of the body of a patient with a nonambient temperature fluid comprising:
    a fluid feed reservoir having a reservoir fluid outlet port, said fluid feed reservoir positioned at a predetermined height;
    a fluid collection reservoir having a reservoir fluid inlet port, said fluid collection reservoir positioned at a predetermined height substantially lower relative to said predetermined height of said fluid feed reservoir;
    a pad positionable on the desired portion of the body, said pad having a pad inlet port, a pad outlet port and a continuous fluid pathway from said pad inlet port to said pad outlet port;
    a fluid inlet line having two ends, a first inlet end connected to said reservoir fluid outlet portion and a second inlet end connected to said pad inlet port;
    a fluid outlet line having two ends, a first outlet end connected to said reservoir fluid inlet port and a second outlet end connected to said pad outlet pad; and
    means attached to said fluid collection reservoir for adjusting said predetermined height of said fluid collection reservoir, wherein said adjustment means comprises a substantially elastic cord.

2. A therapeutic treatment device as recited in claim 1 further comprising:
    a dissociable inlet coupling across said second inlet end and said pad inlet port, thereby rendering said second inlet end dissociable from said pad inlet port; and
    a dissociable outlet coupling across said second outlet end and said pad outlet port, thereby rendering said second outlet end dissociable from said pad outlet port.

3. A therapeutic treatment device as recited in claim 1 wherein said reservoir fluid outlet port is positioned on a lower portion of said fluid feed reservoir.

4. A therapeutic treatment device as recited in claim 1 wherein said fluid feed reservoir has a resealable opening in the upper portion of said fluid feed reservoir for charging treatment fluid or ice to said reservoir.

5. A therapeutic treatment device as recited in claim 1 wherein said fluid feed reservoir is a pliant collapsible pouch.

6. A therapeutic treatment device as recited in claim 1 further comprising an insulative sheath surrounding said inlet and outlet lines.

7. A therapeutic treatment device as recited in claim 1 further comprising a stand having means for removably suspending said fluid feed and fluid collection reservoirs therefrom.

8. A therapeutic treatment device as recited in claim 1 wherein said reservoir fluid inlet port is positioned on a lower portion of said fluid collection reservoir, said fluid collection reservoir has a resealable opening in the upper portion thereof for charging treatment fluid or ice to said reservoir, and said fluid collection reservoir is a pliant collapsible pouch.

9. A therapeutic treatment device as recited in claim 8 wherein said fluid feed and fluid collection reservoirs may be used interchangeably with one another.

10. A device for therapeutically treating a desired portion of the body of a patient with a nonambient temperature fluid comprising:
    a first fluid reservoir having a first reservoir port;
    a second fluid reservoir having a second reservoir port;
    a pad positionable on the desired portion of the body, said pad having a first pad port, a second pad port and a continuous fluid pathway between said first and second pad ports;
    a first fluid line having two ends, a first end connected to said first reservoir port and a second end connected to said first pad port;
    a second fluid line having two ends, a first end connected to said second reservoir port and a second end connected to said second pad port; and
    means comprising a first elastic cord attached to said first fluid reservoir and a second elastic cord attached to said second fluid reservoir for maintaining said first fluid reservoir at a different height than the height of said second fluid reservoir to provide a fluid-containing higher reservoir.

11. A therapeutic treatment device as recited in claim 10 wherein said first and second fluid reservoirs are interchangeable as said fluid-containing higher reservoir.

12. A therapeutic treatment device as recited in claim 10 wherein said height maintaining means further comprises a stand from which said first and second cords are suspendable.

13. A device for therapeutically treating a desired portion of the body of a patient with a nonambient temperature fluid comprising:
    a first fluid reservoir having a first reservoir port positioned on a lower portion of said first reservoir;
    a first elastic cord attached to said first fluid reservoir;
    a second fluid reservoir having a second reservoir port positioned on a lower portion of said second reservoir;
    a second elastic cord attached to said second fluid reservoir;
    a pad positionable on the desired portion of the body, said pad having a first pad port, a second pad port and a continuous fluid pathway between said first and second pad ports;
    a first fluid line having two ends, a first end connected to said first reservoir port and a second end connected to said first pad port; and
    a second fluid line having two ends, a first end connected to said second reservoir port and a second end connected to said second pad port.

* * * * *